United States Patent
Zarafshani et al.

(10) Patent No.: US 12,036,405 B2
(45) Date of Patent: Jul. 16, 2024

(54) SYSTEM AND METHOD OF ELECTRIC-INDUCED ACOUSTIC TOMOGRAPHY FOR ELECTROTHERAPY MONITORING

(71) Applicant: The Board of Regents of the University of Oklahoma, Norman, OK (US)

(72) Inventors: Ali Zarafshani, Norman, OK (US); Liangzhong Xiang, Norman, OK (US); Bin Zheng, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 868 days.

(21) Appl. No.: 16/362,238

(22) Filed: Mar. 22, 2019

(65) Prior Publication Data
US 2019/0290903 A1    Sep. 26, 2019

Related U.S. Application Data

(60) Provisional application No. 62/647,124, filed on Mar. 23, 2018.

(51) Int. Cl.
*A61B 8/13*    (2006.01)
*A61K 9/00*    (2006.01)
(Continued)

(52) U.S. Cl.
CPC .............. *A61N 1/327* (2013.01); *A61B 8/13* (2013.01); *A61K 9/0009* (2013.01); *A61N 1/08* (2013.01);
(Continued)

(58) Field of Classification Search
CPC .... A61N 1/327; A61N 1/3603; A61N 1/0412; A61B 8/13
See application file for complete search history.

(56) References Cited

U.S. PATENT DOCUMENTS

| 6,645,144 B1 * | 11/2003 | Wen ................... G01N 29/0609 600/407 |
| 2008/0132884 A1 * | 6/2008 | Rubinsky ........... A61B 18/1477 606/50 |

(Continued)

FOREIGN PATENT DOCUMENTS

| WO | WO-9800732 A1 * | 1/1998 | ........... A61B 5/0093 |

OTHER PUBLICATIONS

Matej Kranjc et al., In Situ Monitoring of Electric Field Distribution in Mouse Tumor during Electroporation, Radiology: vol. 274, No. 1 (Jan. 2015); available at https://pubs.rsna.org/doi/pdf/10.1148/radiol.14140311 (Year: 2015).*

(Continued)

*Primary Examiner* — Patricia J Park
(74) *Attorney, Agent, or Firm* — Conley Rose, P.C.; Grant Rodolph; Jonathan K. Polk

(57) ABSTRACT

A method and system for monitoring an electrotherapy treatment applied to a subject in need of such therapy. An ultrasound transducer array is positioned adjacent a tissue of the subject to which the electrotherapy treatment is to be applied. The electrotherapy treatment is administered to the tissue as a plurality of ultra-short electric pulses which generate an electric field in the vicinity of the tissue. The ultrasound transducer array detects acoustic signals which are induced by the electric field. The detected acoustic signals are then used to construct tomographic images which represent the electric field generated by the electrotherapy treatment during real-time.

30 Claims, 10 Drawing Sheets

(51) Int. Cl.
    *A61N 1/08*     (2006.01)
    *A61N 1/30*     (2006.01)
    *A61N 1/32*     (2006.01)
    *A61N 1/36*     (2006.01)
    *A61B 6/03*     (2006.01)
    *A61N 1/04*     (2006.01)

(52) U.S. Cl.
    CPC ............. *A61N 1/30* (2013.01); *A61N 1/3603* (2017.08); *A61B 6/03* (2013.01); *A61N 1/0412* (2013.01); *A61N 1/36142* (2013.01)

(56) References Cited

U.S. PATENT DOCUMENTS

| | | | | |
|---|---|---|---|---|
| 2009/0254019 | A1* | 10/2009 | Gehl | A61B 18/1477 604/21 |
| 2010/0261994 | A1* | 10/2010 | Davalos | A61B 18/1477 600/407 |
| 2014/0378964 | A1* | 12/2014 | Pearson | A61B 18/1477 606/41 |
| 2016/0157932 | A1* | 6/2016 | Nuccitelli | A61N 1/40 604/20 |
| 2017/0266438 | A1* | 9/2017 | Sano | A61B 18/1477 |
| 2017/0333112 | A1* | 11/2017 | Nuccitelli | A61B 18/14 |
| 2019/0083187 | A1* | 3/2019 | Danitz | A61B 18/1402 |

OTHER PUBLICATIONS

Yair Granot et al., In vivo imaging of irreversible electroporation by means of electrical impedance tomography. Physics in medicine and biology. 54. 4927-43. 10.1088/0031-9155/54/16/006. (2009) (Year: 2009).*

Zarafshani, Ali, et al.; "Electroacoustic Tomography (EAT): Linear Scanning with a Single Element Transducer"; Proceedings vol. 10955; Medical Imaging 2019: Ultrasonic Imaging and Tomography; Feb. 16-21, 2019; San Diego, California; 6 pages.

Zarafshani, Ali, et al.; "Electroacoustic Tomography System with Nanosecond Electric Pulse Excitation Source"; Proceedings vol. 10955; Medical Imaging 2019: Ultrasonic Imaging and Tomography; Feb. 16-21, 2019; San Diego, California; 6 pages.

Zarafshani, Ali, et al.; "Real-Time, In Situ Monitoring of Nanoporation Using Electric Field-Induced Acoustic Signal"; Proceedings vol. 10495; Biophotonics and Immune Response XIII; Jan. 27-Feb. 1, 2018; 7 pages.

Zhang, Yue, et al.; "MR Imaging to Assess Immediate Response to Irreversible Electroporation for Targeted Ablation of Liver Tissues: Preclinical Feasibility Studies in a Rodent Model"; Radiology; Aug. 2010; vol. 256, No. 2; 9 pages.

Zhou, Yong, et al.; "Tutorial on Photoacoustic Tomography"; Journal of Biomedical Optics; Jun. 2016; vol. 21; 15 pages.

Zimmermann, U.; "Electric Field-Mediated Fusion and Related Electrical Phenomena"; Biochimica et Biophysica Acta; Nov. 30, 1982; 51 pages.

Al-Sakere, Bassim, et al.; "Tumor Ablation with Irreversible Electroporation"; PLoS One; Nov. 2007; Issue 11; 8 pages.

Andreason, Grai L., et al.; "Introduction and Expression of DNA Molecules in Eukaryotic Cells by Electroporation"; BioTechniques; 1988; vol. 6, No. 7; 10 pages.

Chu, Gilbert, et al.; "Electroporation for the Efficient Transfection of Mammalian Cells with DNA"; Nucleic Acids Research; 1987; vol. 15, No. 3; 16 pages.

Davalos, Rafael V., et al.; "A Feasibility Study for Electrical Impedance Tomography as a Means to Monitor Tissue Electroporation for Molecular Medicine"; IEEE Transactions on Biomedical Engineering; Apr. 2002; vol. 49, No. 4; 4 pages.

Davalos, Rafael V., et al.; "Implications and Considerations of Thermal Effects When Applying Irreversible Electroporation Tissue Ablation Therapy"; The Prostate; 2015; vol. 75; 5 pages.

Davalos, R. V., et al.; "Tissue Ablation with Irreversible Electroporation"; Annals of Biomedical Engineering; Feb. 2005; vol. 33, No. 2; 9 pages.

Dev, Sukhendu B., et al.; "Medical Applications of Electroporation"; IEEE Transactions on Plasma Science; Feb. 2000; vol. 28, No. 1; 18 pages.

Edhemovic, Ibrahim, et al.; "Intraoperative Electrochemotherapy of Colorectal Liver Metastases"; Journal of Surgical Oncology; 2014; vol. 110; 8 pages.

Gebauer, Bastian, et al.; "Impedance-Acoustic Tomography"; SIAM Journal on Applied Mathematics; Jan. 2008; vol. 69, No. 2; 13 pages.

Gehl, J.; "Electroporation: Theory and Methods, Perspectives for Drug Delivery, Gene Therapy and Research"; Acta Physiol Scand; 2003; vol. 177; 11 pages.

Granot, Yair, et al.; "In Vivo Imaging of Irreversible Electroporation by means of Electrical Impedance Tomography"; Physics in Medicine and Biology; 2009; vol. 54; 18 pages.

Guo, Yang, et al.; "Irreversible Electroporation in the Liver: Contrast-Enhanced Inversion-Recovery MR Imaging Approaches to Differentiate Reversibly Electroporated Penumbra from Irreversibly Electroporated Ablation Zones"; Radiology; Feb. 2011; vol. 258, No. 2; 8 pages.

Heller, Richard, et al.; "Clinical Applications of Electrochemotherapy"; Advanced Drug Delivery Reviews; 1999; vol. 35; 11 pages.

Heller, Richard, et al.; "Phase I/II Trial for the Treatment of Cutaneous and Subcutaneous Tumors Using Electrochemotherapy"; American Cancer Society; Mar. 1, 1996; vol. 77, No. 5; 8 pages.

Hemmler, Roland, et al.; "Nanopore Unitary Permeability Measured by Electrochemical and Optical Single Transporter Recording"; Biophysical Journal; Jun. 2005; vol. 88, No. 6, 8 pages.

Hjouj, Mohammad, et al.; "Magnetic Resonance Imaging Characteristics of Nonthermal Irreversible Electroporation in Vegetable Tissue"; Journal of Membrane Biology; Jul. 2010; vol. 236; 11 pages.

Jossinet, Jacques, et al.; "A Review of Parameters for the Bioelectrical Characterization of Breast Tissue"; Annals New York Academy of Sciences; Apr. 20, 1999; vol. 873, No. 1; 12 pages.

Kinosita Jr., Kazuhiko, et al.; "Hemolysis of Human Erythrocytes by a Transient Electric Field"; Proc. Natl, Acad. Sci. USA; May 1977; vol. 74, No. 5; 5 pages.

Kranjc, Matej, et al.; "In Situ Monitoring of Electric Field Distribution in Mouse Tumor during Electroporation"; Radiology; Jan. 2015; vol. 274, No. 1; 9 pages.

Kranjc, Matej, et al.; "Predicting Irreversible Electroporation-Induced Tissue Damage by Means of Magnetic Resonance Electrical Impedance Tomography"; Scientific Reports; Sep. 7, 2017; vol. 7; 10 pages.

Lee, Edward, W., et al.; "Advanced Hepatic Ablation Technique for Creating Complete Cell Death: Irreversible Electroporation"; Radiology; May 2010; vol. 255, No. 2; 8 pages.

Mahmood, Faisal, et al.; "Diffusion-Weighted MRI for Verification of Electroporation-Based Treatments"; J. Membrane Biol.; 2011; vol. 240; 8 pages.

Marty, Michel, et al.; "Electrochemotherapy—An Easy, Highly Effective and Safe Treatment of Cutaneous and Subcutaneous Metastases: Results of ESOPE (European Standard Operating Procedures of Electrochemotherapy) Study"; EJC Supplements; Nov. 2006; vol. 4, No. 11; 11 pages.

Miklavcic, Damijan, et al.; "The Importance of Electric Field Distribution for Effective in Vivo Electroporation of Tissues"; Biophysical Journal; May 1998; vol. 74; 7 pages.

Mir, Lluis M., et al.; "Electrochemotherapy Potentiation of Antitumour Effect of Bleomycin by Local Electric Pulses"; Eur. J. Cancer; 1991; vol. 27, No. 1; 5 pages.

Muratori, Claudia, et al.; "Electrosensitization Assists Cell Ablation by Nanosecond Pulsed Electric Field in 3D Cultures"; Scientific Reports; Mar. 18, 2016; vol. 6; 9 pages.

Neumann, E., et al.; "Gene Transfer into Mouse Lyoma Cells by Electroporation in High Electric Fields"; The EMBO Journal; 1982; vol. 1, No. 7; 5 pages.

(56) References Cited

OTHER PUBLICATIONS

Neumann, Eberhard, et al.; "Permeability Changes Induced by Electric Impulses in Vesicular Membranes"; Journal of Membrane Biology; Dec. 1972; vol. 10; 15 pages.
Orlowski, Stephane, et al.; "Transient Electropermeabilization of Cells in Culture"; Biochemical Pharmacology; 1988; vol. 37, No. 24; 7 pages.
Prausnitz, Mark R., et al.; "Electroporation of Mammalian Skin: A Mechanism to Enhance Transdermal Drug Delivery"; Proc. Natl. Acad. Sci. USA; Nov. 1993; vol. 90; 5 pages.
Robinson, M. P., et al.; "New Materials for Dielectric Simulation of Tissues"; Physics in Medicine and Biology; 1991; vol. 36, No. 12; 9 pages.
Rolong, Andrea, et al.; "History of Electroporation"; Irreversible Electroporation in Clinical Practice; Springer International Publishing AG 2018; 29 pages.
Rols, Marie-Pierre, et al.; "In Vivo Electrically Mediated Protein and Gene Transfer in Murine Melanoma"; Nature Biotechnology; Feb. 1998; vol. 16; 4 pages.
Satkauska, Saulius, et al.; "Mechanisms of in Vivo DNA Electrotransfer: Respective Contributions of Cell Electropermeabilization and DNA Electrophoresis"; Molecular Therapy; Feb. 2002; vol. 5, No. 2; 8 pages.
Schmidt, Carl R., et al.; "Real-Time Ultrasound Imaging of Irreversible Electroporation in a Porcine Liver Model Adequately Characterizes the Zone of Cellular Necrosis"; International Hepato-Pancreato-Biliary Association; 2011; 5 pages.
Sun, Yao, et al.; "Enahancing Tissue Permeability with MRI Guided Preclinical Focused Ultrasound System in Rabbit Muscle: From Normal Tissue to VX2 Tumor"; J. Control Release; Jun. 28, 2017; 19 pages.
Surowiec, Andrzej J., et al. "Dielectric Properties of Breast Carcinoma and the Surrounding Tissues"; IEEE Transactions on Biomedical Engineering; Apr. 4, 1988; vol. 35, No. 4; 7 pages.
Teissie, Justin, et al.; "Electric Field Induced Transient Pores in Phospholipid Bilayer Vesicles"; Biochemistry; 1981; vol. 20; 7 pages.
Thomas, Kirk, R. et al.; "Site-Directed Mutagenesis by Gene Targeting in Mouse Embryo-Derived Stem Cells"; Cell; Nov. 6, 1987; vol. 51; 10 pages.
Van Den Bos, Willemien, et al.; "Thermal Energy During Irreversible Electroporation and the Influence of Different Ablation Parameters"; Journal of Vascular and Interventional Radiology; Dec. 2015; 12 pages.
Van Gemert, Martin J. C., et al.; "Irreversible Electroporation: Just Another Form of Thermal Therapy?"; The Prostate; 2015; vol. 75; 4 pages.
Mncelette, Rebecca L., et al.; "Thresholds for Phosphatidylserine Externalization in Chinese Hamster Ovarian Cells following Exposure to Nanosecond Pulsed Electrical Fields (nsPEF)"; PLOS One; Apr. 2013; vol. 8, Issue 4; 12 pages.
Wagstaff Peter G.K., et al.; "Irreversible Electroporation: State of the Art"; OncoTargets and Therapy; Apr. 22, 2016; 10 pages.
Wagstaff, Peter G.K., et al.; "Irreversible Electroporation of the Porcine Kidney: Temperature Development and Distribution"; Urologic Oncology: Seminars and Original Investigations; 2015; vol. 33; 7 pages.
Wang, Lihong V., et al.; "Photoacoustic Tomography: In Vivo Imaging from Organelles to Organs"; Science; Mar. 23, 2012; vol. 335, No. 6075; 6 pages.
Wang, Lihong V.; "Tutorial on Photoacoustic Microscopy and Computed Tomography"; IEEE Journal of Selected Topics in Quantum Electronics; Jan./Feb. 2008; vol. 14, No. 1; 9 pages.
Weaver, James C., et al.; "Theory of Electroporation: A Review"; Bioelectrochemistry and Bioenergetics; 1996; vol. 41; 26 pages.
Xiong, Xiaobing, et al.; "Remote Spatiotemporally Controlled and Biologically Selective Permeabilization of Blood-Brain Barrier"; J. Control Release; Nov. 10, 2015; vol. 217; 18 pages.
Zarafshani, Ali, et al.; "Real-Time In-Situ Monitoring of Electrotherapy Process Using Electric Pulse-Induced Acoustic Tomography (EpAT)"; Proceedings vol. 10573; Medical Imaging 2018: Physics of Medical Imaging; Feb. 10-15, 2018; Houston, Texas, 8 pages.
Zarafshani, Ali, et al.; "Electric-Field Induced Acoustic Tomography (EfAT) for In-Situ Monitoring of Tumor Ablation During Irreversible/Reversible Electroporation"; 2018 RSNA Annual Meeting; 104th Scientific Assembly and Annual Meeting; Nov. 25-30, 2018; McCormick Place, Chicago; 1 page.

\* cited by examiner

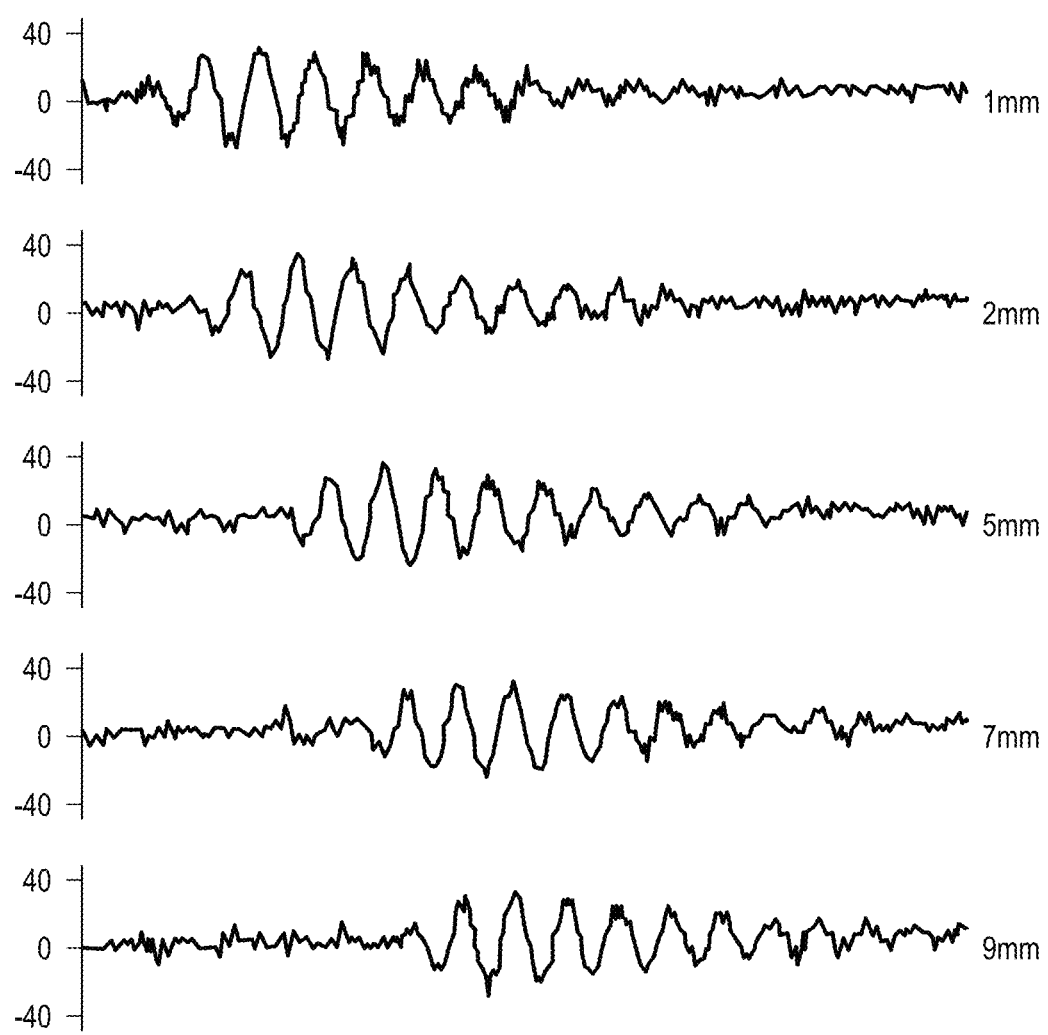

SYSTEM AND METHOD OF ELECTRIC-INDUCED ACOUSTIC TOMOGRAPHY FOR ELECTROTHERAPY MONITORING

CROSS-REFERENCE TO RELATED APPLICATIONS

This application claims priority to U.S. provisional patent application No. 62/647,124 filed on Mar. 23, 2018, by The Board of Regents of the University of Oklahoma and titled "System and Method of Electric-Induced Acoustic Tomography for Electrotherapy Monitoring," which is incorporated by reference.

STATEMENT REGARDING FEDERALLY SPONSORED RESEARCH OR DEVELOPMENT

Not applicable.

BACKGROUND

The use of electrical energy in therapy or electrotherapy is rapidly growing in physiotherapy (e.g., muscular electrostimulation), chemotherapy (e.g., ECT in cancer treatment), and microbiology (e.g., nanopore sequencing as an electropermobilization of drugs, or electrogenetransfer). The technique uses an ultra-short (e.g., μs to ns) and intense (around a few hundred volts) EP to establish an electric field. This increases membrane permeability and allows non-permeant drugs, genes, or DNA access to the cell interior (cytosol) via nanopores in the cell plasma membrane. This process can disrupt cellular homeostasis, transfer anticancer drugs, or facilitate gene electro transfer. Furthermore, this is the general mechanism for reversible and irreversible electroporation, which is a soft tissue ablation technique.

The applied electric field produces cell fusion and electroporation, which can be used to address pressing current challenges related to health and biotechnological processes. Electroporation (electropermeabilization) is a natural phenomenon involving increased cell membrane permeability during exposure to high-voltage electrical pulses. A number of different proteins in the cell membrane act as channels and pathways (nanoporations) for transporting specific molecules across the membrane during the high-voltage, ultrashort EP. Electroporation allows molecules to either permeate into the cell or leave the cell, which is not possible under normal circumstances for many important molecules. The nanoporation of the membrane in reversible and irreversible electroporation modes utilizes ultra-short, high-voltage EPs. Increasing the effectiveness of techniques utilizing electroporation, such as chemotherapy, gene therapy, and microbiology processes, would be possible by having real-time, in-situ monitoring of electroporation.

In terms of pathology, the numbers of treatments using nanopore sequencing as an electropermobilization technique and ECT treatment are increasing. The majority of the cases that use ECT are for treating breast cancer tumors, metastasis of skin and non-skin origin, cell carcinomas with various types of tumors, as well as keloids. But the success of the treatment is still questionable and there is no standard in terms of number of applications related to size and origin of the tumor as well as intensity of electric field. Real-time, in-situ monitoring of electric field distribution would be useful in assessing and evaluating the success of the procedure.

However, the number of applications of the electric field, intensity of EPs, and electric field distribution based on number of electrodes, which are consequently introduced by such techniques, has attracted significant concern about their safety issues and the efficacy of the application. Recent research has shown a strong correlation between the electric field distribution, effectiveness of the treatment, and sensitivity of electric field stimulation. This defines the need for modelling of safety precautions and pretreatment plans to predict treatment response. It is also important to have in-situ monitoring to offer fast feedback for electrotherapy procedures by characterizing the influence of an electric field for analyzing the electric field distribution and electroporation process.

BRIEF DESCRIPTION OF THE DRAWINGS

Several embodiments of the present disclosure are hereby illustrated in the appended drawings. It is to be noted, however, that the appended drawings only illustrate several embodiments and are therefore not intended to be considered limiting of the scope of the present disclosure. The figures are not necessarily to scale and certain features and certain views of the figures may be shown as exaggerated in scale or in schematic in the interest of clarity and conciseness.

FIG. 4A shows acoustic waves detected when the ultrasonic transducer probe is moved from 1 mm to 9 mm (at 1 μs, 800 V pulse) from the sample target.

DETAILED DESCRIPTION

Figure 1:
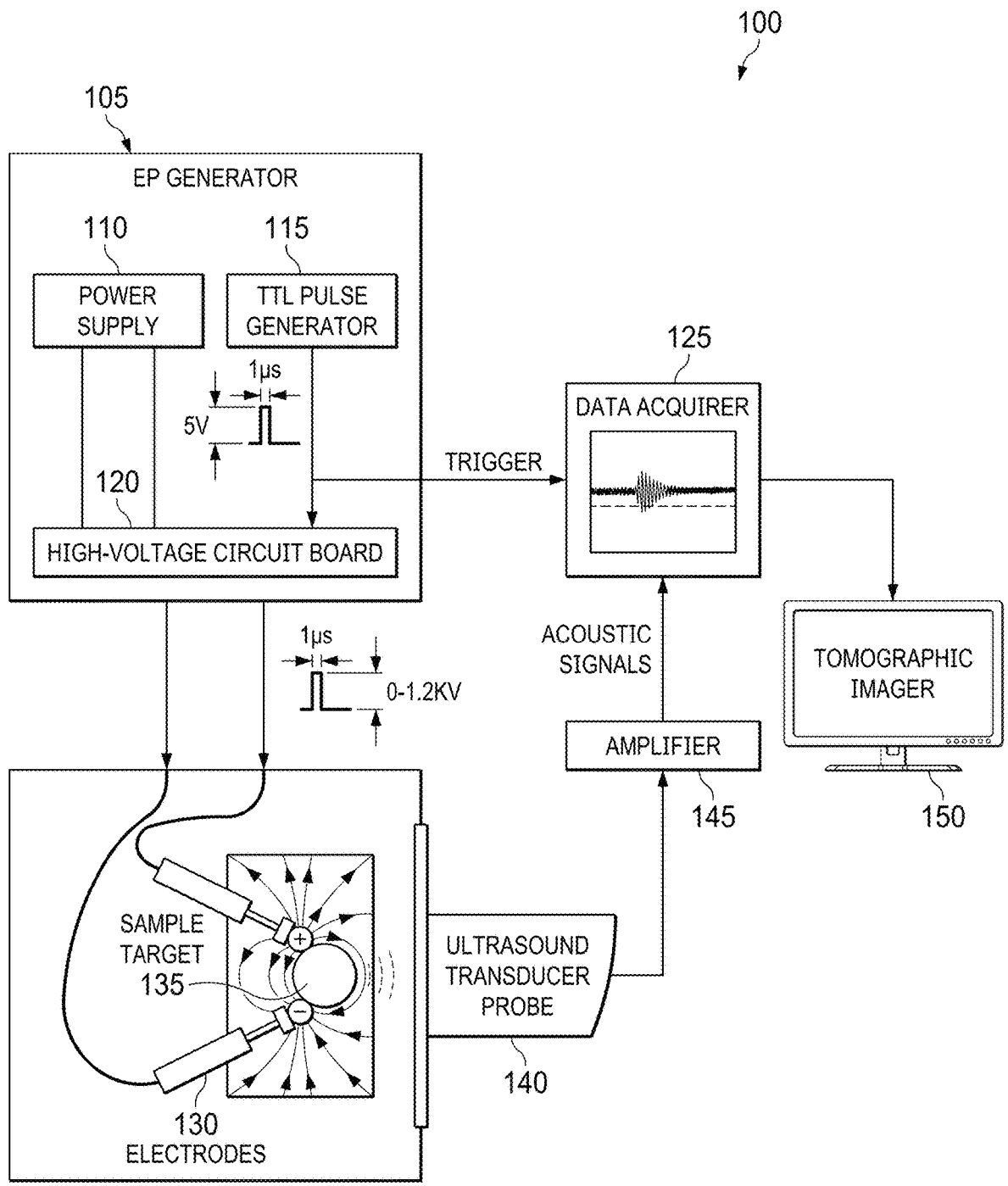
FIG. 1 shows an EAT system constructed in accordance with the present disclosure.

Currently available techniques for characterization, determination, and monitoring of the electric field distribution such as confocal microscopy, MRI, ultrasound imaging, EIT, and MREIT require expensive and complex equipment. The top three desired features in characterization of the electrotherapy process include accuracy of the results, the ability of real-time monitoring, and possibility for corrective intervention. However, currently, all the monitoring techniques for clinical application of electrotherapy are only for pre-and post-stimulation exposure and do not include processes for real-time monitoring of the electric field distribution and electroporation process. There is also no technique capable of giving critical feedback in real time. In addition, it usually requires highly accurate and high-resolution techniques to analyze the electric field distribution. Thus, there is an unmet need in the field for reliable, real-time, in-situ monitoring of the electric field distribution and electrical properties during electrotherapy processes such as electroporation in order to minimize their harmfulness to healthy cells and maximize their effect on target cells. It is to addressing this need that the present disclosure is directed.

The present disclosure describes an EAT system and method for using electroacoustical phenomena to produce high-resolution, high-contrast imaging for real-time monitoring of electrotherapy applications. EAT may also be referred to as EfAT or EpAT. This enables using in-situ guidance images based on electric field distribution and electric conductivity of the treated targets to identify the targets and determine the accuracy of treatment during a treatment procedure. In certain embodiments, the system and method are used to perform real-time monitoring and characterization of the electric field stimulation used in electrotherapies, such as, but not limited to, drug delivery systems, cell treatments, tissue ablation, and the process of apoptosis. In at least one embodiment, the system and methods disclosed herein provide a standard innovative methodology for real-time, in-situ monitoring of electrotherapy procedures based on EAT. The novel system and methods provide an innovative technology which can establish real-time monitoring of the electric field distributions based on conversion of the electrical phenomena used in the clinical treatments.

Advantages of the presently disclosed system and methods include for example, (1) real-time, fast-feedback, quickly correctable, low-cost, non-invasive, high-sensitivity, label-free, and accurate characterizations of electrotherapy applications, such as the electroporation process for addressing cell behavior and response that are stimulated from the outside; (2) an answer to the need created by the treatment of cancer tumors which vary in size, location, and shape; (3) a standard innovative methodology for in-situ monitoring of electrotherapy procedures where safety and effectiveness of the treatment are essential; (4) applicability of the system and method to a variety of situations, with variation of intensity and frequency of electric field exposure; (5) the use in clinician training programs for those who want to be trained with the knowledge of efficiency of treatment; (6) the use as an add-on to existing techniques to enhance their accuracy or functionality as a competitive advantage; and (7) the ability of the entire measurement system to be miniaturized, rendering it applicable to a variety of situations.

In at least one embodiment, the present disclosure is directed to a method and system for monitoring an electrotherapy treatment applied to a subject in need of such therapy. An ultrasound transducer probe, which may be an array and referred to as an ultrasonic transducer probe or simply an ultrasonic transducer, is positioned adjacent a tissue of the subject to which the electrotherapy treatment is to be applied. The electrotherapy treatment is administered to the tissue as a plurality of ultra-short electric pulses (EPs) which generate an electric field in the vicinity of the tissue. The ultrasound transducer probe detects acoustic signals which are induced by the electric field. Specifically, the EPs may raise the temperature of the tissue and thus cause the tissue to expand. That expansion may generate the acoustic signals. The detected acoustic signals are then used to construct tomographic images which represent the electric field generated by the electrotherapy treatment during real time.

In one non-limiting embodiment, the present disclosure includes a method of monitoring an electrotherapy treatment applied to a subject in need of such treatment by positioning an ultrasound transducer probe adjacent to a tissue of a subject; administering the electrotherapy treatment to the tissue as a plurality of ultra-short EPs; detecting, using the ultrasound transducer probe, acoustic signals induced by an electric field generated in a vicinity of the tissue in response to the electrotherapy treatment; and constructing tomographic images from the acoustic signals while the electrotherapy treatment is being applied to the subject, the tomographic images representing a location of the electric field in the tissue. The electrotherapy treatment may be, for example, is electroporation, electrochemotherapy, or muscular electrostimulation. The electrotherapy treatment may be repositioned and/or adjusted based on the location of the electric field represented in the tomographic images.

In another non-limiting embodiment, the present disclosure includes an electric-field-inducted acoustic tomography (EAT) system which includes an electric pulse (EP) generator configured to generate a plurality of ultra-short EPs; electrodes coupled to the EP generator and configured to administer an electrotherapy treatment to a tissue of a subject via the ultra-short EPs; an ultrasound transducer probe configured to detect acoustic signals induced by an electric field generated in the tissue of the subject in response to the electrotherapy treatment; and a tomographic imager configured to construct tomographic images from the acoustic signals induced by the electric field, wherein the tomographic images represent the electric field, and wherein the tomographic imager is configured to construct the tomographic images during the electrotherapy treatment to enable monitoring of the electrotherapy treatment. The ultrasound transducer probe may be configured to convert the acoustic signals into electrical signals, and wherein the EAT system further comprises an amplifier coupled to the ultrasound transducer probe, the amplifier configured to amplify the electrical signals to create amplified electrical signals. The EAT system may include a data acquirer coupled to the EP generator, the amplifier, and the tomographic imager and configured to synchronize the ultra-short EPs with the acoustic signals. The EAT system may be configured to enable repositioning and/or adjusting the electrotherapy treatment based on the location of the electric field represented in the tomographic images.

Before further describing various embodiments of the systems and methods of the present disclosure in more detail by way of exemplary description, examples, and results, it is to be understood that the embodiments of the present disclosure are not limited in application to the details as set forth in the following description. The embodiments of the present disclosure are capable of being practiced or carried out in various ways not explicitly described herein. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description. While the present disclosure has been described in terms of particular embodiments, it will be apparent to those of skill in the art that variations may be applied to the apparatus and/or methods and in the steps or in the sequence of steps of the methods described herein without departing from the concept, spirit, and scope of the inventive concepts as described herein. All such similar substitutes and modifications apparent to those having ordinary skill in the art are deemed to be within the spirit and scope of the inventive concepts as disclosed herein.

All patents, published patent applications, and non-patent publications referenced or mentioned in any portion of the present specification are indicative of the level of skill of those skilled in the art to which the present disclosure pertains, and are hereby expressly incorporated by reference in their entirety to the same extent as if the contents of each individual patent or publication was specifically and individually incorporated herein.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. In particular, the following abbreviations may be used herein:

amp-hr: ampere(s)-hour
C: celsius
cm: centimeter(s)
$cm^3$: cubic centimeter(s)
dB: decibel(s)
DC: direct current
DNA: deoxyribonucleic acid
EAT: electric-field-induced acoustic tomography
ECT: electrochemotherapy
EfAT: electric-field-induced acoustic tomography
EIT: electrical impedance tomography
EP: electric pulse
EpAT: electric-pulse-induced acoustic tomography
eV: electron-volt(s)
g: gram(s)
GND: ground
HV: high-voltage
Hz: hertz
J: joule(s)
k: kelvin
kH: kilohenry(s)
kHz: kilohertz
kV: kilovolt(s)
LED: light-emitting diode
mA: milliamp(s)
MHz: megahertz
mK: millikelvin
mm: millimeter(s)
mol: mole
MOSFET: metal-oxide-semiconductor field-effect transistor
MREIT: magnetic resonance EIT
MRI: magnetic resonance imaging
mS: millisiemen(s)
ns: nanosecond(s)
Pa: pascal(s)
pF: picofarad(s)
ps: picosecond(s)
S: siemen(s)
SHVC: specialized high-voltage controller
TTL: transistor-to-transistor logic
V: volt(s)
W: watt(s)
2D: two-dimensional
3D: three-dimensional
μm: micrometer(s)
μs: microsecond(s)
Ω: ohm(s).

As utilized in accordance with the apparatus, methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the terms "at least one" or "plurality" will be understood to include one as well as any quantity more than one, including but not limited to, 2, 3, 4, 5, 6, 7, 8, 9, 10, 15, 20, 30, 40, 50, 100, or any integer inclusive therein, and/or any range described herein. The terms "at least one" or "plurality" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error in a parameter. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value is also meant to encompass, for example, variations of ±20% or ±10%, or ±5%, or ±1%, or ±0.1% from the specified value. As used herein, the term "substantially" means that the subsequently described event, circumstance or parameter completely occurs or that the subsequently described event, circumstance, or parameter occurs to a great extent or degree.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91%, or at least 92%, or at least 93%, or at least 94%, or at least 95%, or at least 96%, or at least 97%, or at least 98%, or at least 99%, of the referenced dimension or measurement (e.g., length).

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Features of any of the embodiments disclosed herein may be combined with features of any of the other embodiments disclosed herein to create a new embodiment.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units (for example where units are picoseconds (µs), nanoseconds (ns), microseconds (µs), volts (V), or Hertz (Hz)) therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein. Any of the embodiments described herein may be combined with any of the other embodiments to create a new embodiment.

The inventive concepts of the present disclosure will be more readily understood by reference to the following examples and embodiments and accompanying drawings, which are included merely for purposes of illustration of certain aspects and embodiments thereof, and are not intended to be limitations of the disclosure in any way whatsoever. Those skilled in the art will promptly recognize appropriate variations of the apparatus, compositions, components, procedures and method shown below.

EXAMPLES

Example 1

Commonly, electrotherapy employs an ultra-short (e.g., in a range of ps to ns to µs) and intense (e.g., in a range of about 100 to 1500 V) EP at a frequency (e.g., in a range of about 10 Hz to about 10 kHz) to create an electric stimulus in the target area. In ECT, this increases membrane permeability, allowing therapeutics such as genes, anticancer drugs, and diagnostic compounds to access the cell cytosol via nanopores in the cell membrane. In order to monitor the electric field distribution during real time, the methods of the present disclosure can use the electric field that is applied in the procedure (e.g., treatment or nanoporation process), to induce acoustic signals which are detected and used to characterize in-situ and real-time monitoring of the electric field distributed in the treated subjects.

An EP generates an electric field, which induces directional acoustic waves, which may also be referred to as acoustic signals. The EP is deposited within a short time pulse width to a sample target, generating acoustic signals which correspond to the electric field. In fact, the acoustic pressure induces high-resolution acoustic waves. These acoustic signals are detected by an ultrasound transducer probe to produce a tomographic image. Thus, the present system and method are referred to as EAT. In EAT, tomographic images are constructed from the ultrasound signals induced by the electric field stimuli, which are detected using an ultrasound transducer probe.

The acoustic signal depends on the flow of electrons through the medium, which is affected by its density and the dielectric characteristics of the medium. A change in the dielectric characteristics of tissue will translate into a corresponding change in the acoustic signal. The acoustic flight time in pulsed excitation provides electrical depth information of the absorbing targets. If a higher frequency transducer and a narrower pulsed electric source are employed in experiments, sub-micrometer spatial resolution imaging of tissue electric properties should be achievable. This unique feature has the potential to enable a 2D electric field-induced acoustic technique as an in-vivo imaging tool to quantitatively measure tissue bioelectrical properties for diagnosis.

FIG. 1 shows an EAT system 100 constructed in accordance with the present disclosure. The EAT system 100 provides real-time, in-situ monitoring of electroporation or other electrotherapies. The EAT system 100 comprises an EP generator 105, a data acquirer 125, electrodes 130, a sample target 135, an ultrasound transducer probe 140, an amplifier 145, and a tomographic imager 150. The EP generator 105 comprises a power supply 110, a TTL pulse generator 115, and a high-voltage circuit board 120. The EP generator 105 may provide high-voltage μs-ns EPs, the power supply 110 may provide high voltages of about 0-1.2 kV, the TTL pulse generator 115 may provide pulses of about 1 μs-100 ns, the amplifier 145 may amplify signals by about 40-60 dB, the high-voltage circuit board 120 may be an SHVC, electrodes 130 may be bipolar electrodes, and the ultrasound transducer probe 140 may be an array of such ultrasound transducer probes.

In operation, the EP generator 105 generates a plurality of ultra-short EPs. The electrodes 130 administer an electrotherapy treatment to the sample target 135 via the ultra-short EPs. The ultrasound transducer probe 140 detects acoustic signals induced by an electric field generated in a vicinity of the sample target 135 in response to the electrotherapy treatment and converts the acoustic signals into electrical signals. The amplifier 145 amplifies the electrical signals to create amplified electrical signals. The data acquirer 125 synchronizes the ultra-short EPs with the acoustic signals. The tomographic imager 150 uses electric signals converted from the acoustic signals to construct tomographic images which represent the electric field being applied to the tissue. The tomographic imager 150 may do so in real time while the electrodes 130 administer the electrotherapy treatment.

Subsequently, the electrodes may continue administration of the electrotherapy treatment to only a most effective area of the tissue, in order to avoid or mitigate damage to surrounding cells of the tissue. The most effective area, i.e., the area of tissue in the vicinity of the applied electric field, is identified from the tomographic images. For instance, a physician or a technician may evaluate the tomographic images and adjust positions of the electrodes 130 to only the most effective area. Likewise, the physician or the technician may evaluate the tomographic images and determine areas of the tissue with no electroporation or incomplete electroporation.

The process of electroporation normally would be carried out by placing the electrodes 130 on the sample target 135, which may be a tissue, such as a tumor, in a subject. The electrodes 130 focus an ultra-short intensive electric field distribution. Non-limiting examples of electric field parameters used in the methods of the present disclosure are in a range of about 1 ps to about 100 μs pulse width (e.g., 1 ps to 10 ps to 100 ps to 1 ns to 10 ns to 100 ns to 1 μs to 10 μs to 100 μs), about 1 V to about 5 kV excitation (e.g., 100 V/cm to about 12 kV/cm), and about 1 Hz to about 100 kHz (e.g., 10 Hz to about 10 kHz) frequency.

The pulse width and voltage level can be adjusted based on real-time requirements. In one non-limiting embodiment, the EP generator 105 uses the power supply 110 when storing an electrical charge for delivery to the sample target 135. The power supply 110 can be served by the TTL pulse generator 115 and connected to the high-voltage circuit board 120. An electroporation system is established by applying an electric field distribution using the electrodes 130 at a specified distance of, for example, 100 μm-10 mm.

Each electrode 130 may be at a different distance. For instance, one electrode 130 may be 100 μm away, and another electrode 130 may be 200 μm away. The level of electrical potential (voltage) and pulse width can be adjusted to generate different electric field (E) excitations within a distance (d), (E=V/d), where E is the magnitude of the electric field between the electrodes 130, V is the potential difference between the electrodes 130, and d is the separation of the electrodes 130, resulting in different acoustic signals corresponding to the variation of temperature. The resulting mK temperature rise produces a pressure wave that is detectable by the ultrasound transducer probe 140. This provides a real-time signal from interior processes with no additional source and add-on imaging modality. Acoustic signals can be picked up by the ultrasound transducer probe arranged in 2D or 3D structures providing a real-time 2D or 3D imaging.

The TTL pulse generator 115 generates a TTL pulse (TTL signal) that is connected to drive the high-voltage circuit board 120 to energize the two electrodes 130. This TTL signal is also connected to the ultrasound transducer probe 140 for triggering the detection of ultrasound signals. The EP generator 105 is connected to the two electrodes 130 with a potential difference (bi-polar pulses) with an adjustable setup to produce a variable voltage-to-distance ratio (V/cm). A different electric field distribution was created by varying the pulse width (between μs and ns) and voltage intensity (from 0 to 1.2 kV).

Figure 2:
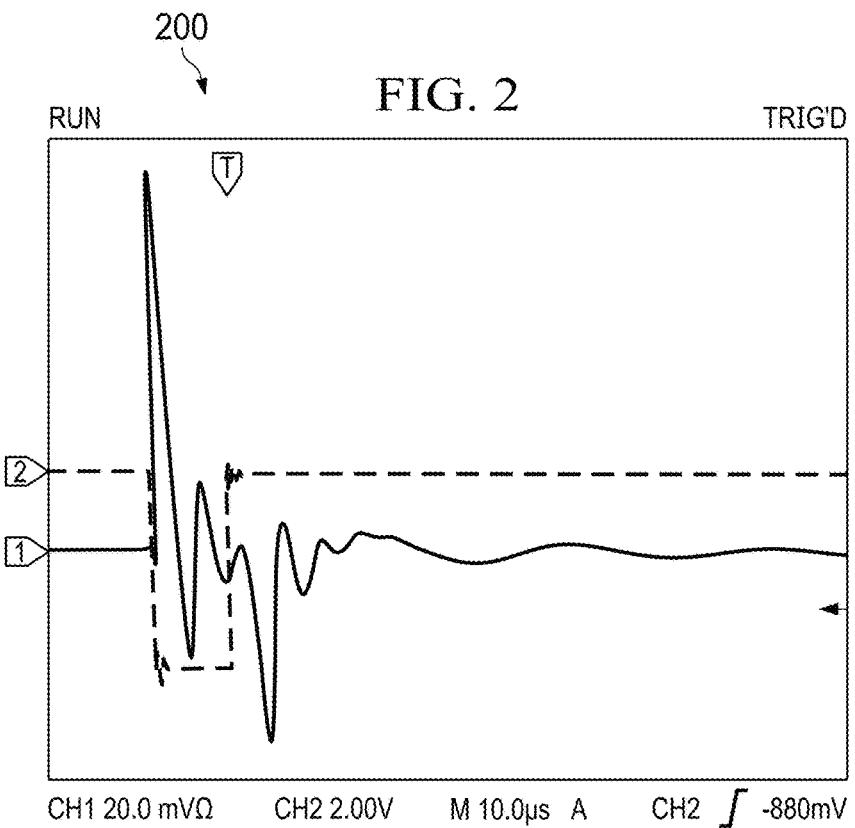
FIG. 2 shows an oscilloscope image of an EP of 1 μs duration used as a trigger to detect an electric field using the EAT system of FIG. 1.

FIG. 2 shows an oscilloscope image 200 of an EP of 1 μs duration used as a trigger to detect an electric field using the EAT system 100 of FIG. 1. The EP is shown as channel 2, and the electric field is shown as channel 1. The experience results in three dimensions of x-, y-, and z-axes obtained when the EP produces an acoustic signal that is a function of dielectric properties of the sample target 135. Therefore, the obtained signals can be demonstrated as an example of electric field-induced acoustic waves as shown in FIG. 3.

Figure 3:
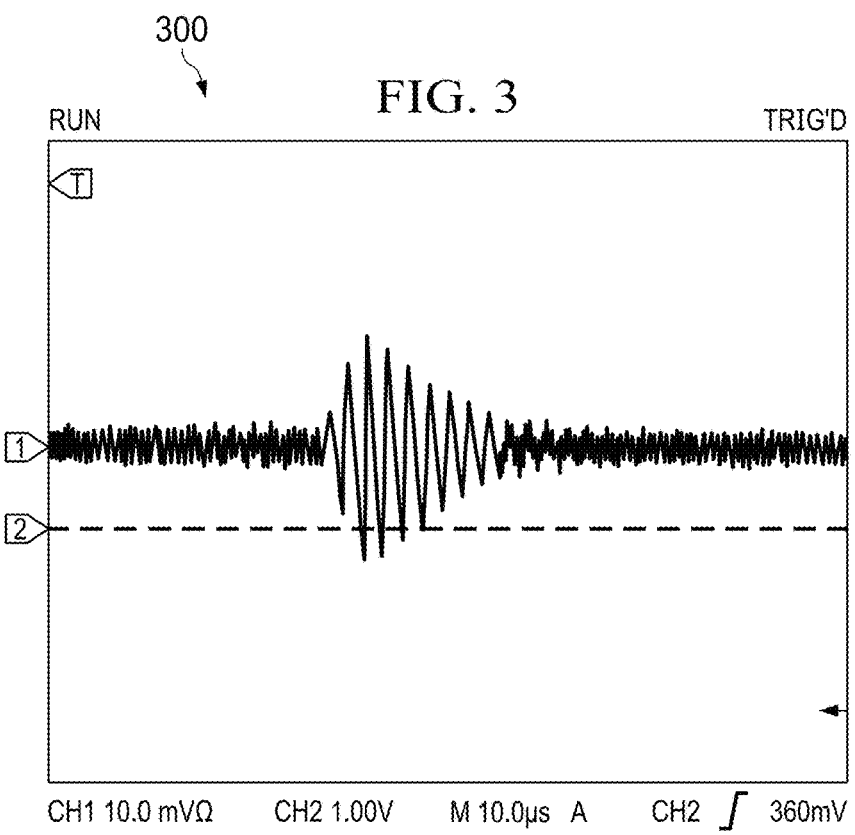
FIG. 3 shows an oscilloscope image of an acoustic wave generated by the EP applied to the sample target as detected by the ultrasound transducer probe of FIG. 1.

FIG. 3 shows an oscilloscope image 300 of an acoustic wave generated by the EP applied to the sample target 135 as detected by an ultrasound transducer probe 140 of FIG. 1. The electric field exposure was established with a 1 μs pulse and an applied voltage of 1.2 kV to generate an electric field of approximately 17.15 kV/cm, which is typical of electric field exposure used in clinical electrotherapy.

Example 2

The EAT system 100 was used to generate high-intensity, ultra-short EPs (ns to μs) to apply an electric stimulus in the sample target 135 under test. As noted above, the TTL signal is also connected to the ultrasound transducer probe 140 for triggering the detected ultrasound signals. An adjustable setup is designed to produce a variable voltage-to-distance ratio. In this setup, different electric field distributions were created by varying the EP width between 100 ns and 10 μs (with a falling and rising time of a minimum of 2.9 ns), varying the voltage intensity from 0 to 1.2 kV and varying the distance between the electrodes. The system was implemented with different pulse durations and applied voltages, yielding an electric field of 12 kV/cm at an inter-electrode distance of 1 mm to determine the effect of electric field distribution corresponding to acoustic signals. These acoustic signals were detected by the ultrasound transducer probe 140 from the sample target 135. An EP of 1 μs was used as a trigger (channel-2) to detect the electric field (channel-1), as measured on an oscilloscope. The acoustic signal was observed when the μs EP was exposed to sample target 135.

The acoustic signal was amplified by 60 dB with an average acquisition mode of 4 times. The electric field exposure was established with a 1 μs pulse and an applied voltage of 1.2 kV to generate an electric field of approximately 17.15 kV/cm, which is typical of electric field exposure used in clinical electrotherapy. The results of the experiment are obtained in three dimensions, x, y, and z, when the μs EP produces an acoustic signal that is a function of dielectric properties of the subject. The electric field exposure location was changed in three directions when moving the electrodes' 130 location with respect to the ultrasound transducer probe 140 to different positions (left-right, up-down, and near-far field).

FIG. 4A shows acoustic waves 400 detected when the ultrasound transducer probe 140 is moved from 1 mm to 9 mm (at 1 μs, 800 V pulse) from the sample target 135. FIG. 4A demonstrates variations of the electric field distribution corresponding to the location of, and distance from, the sample target 135 and corresponding to the intensity of the electric field. The acoustic signals detected from different distances with the same 1 μs EP pulse and 800 V intensity are included to demonstrate the feasibility of the disclosed method. This indicated the relative location of the electric field and the movement of the ultrasound transducer probe 140 in the x-axis direction. The imaging technique has the advantage of directional properties of the electric field and the induced acoustic wave.

Figure 4B:
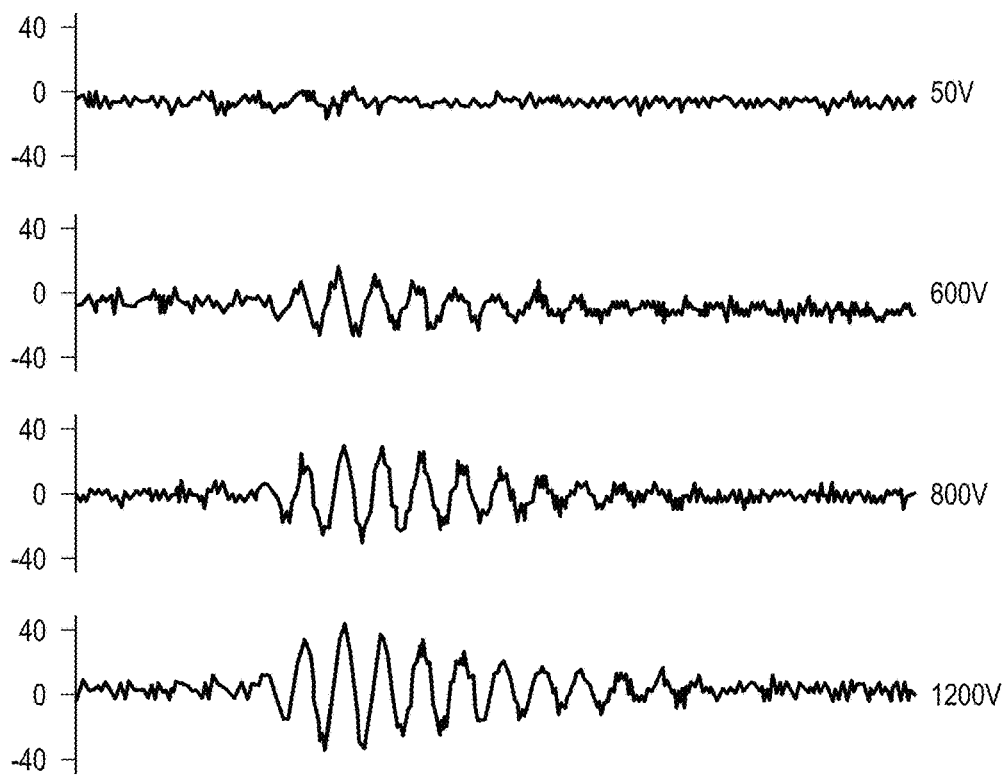
FIG. 4B shows acoustic waves detected when the electric field increases in intensity.
Figure 4C:
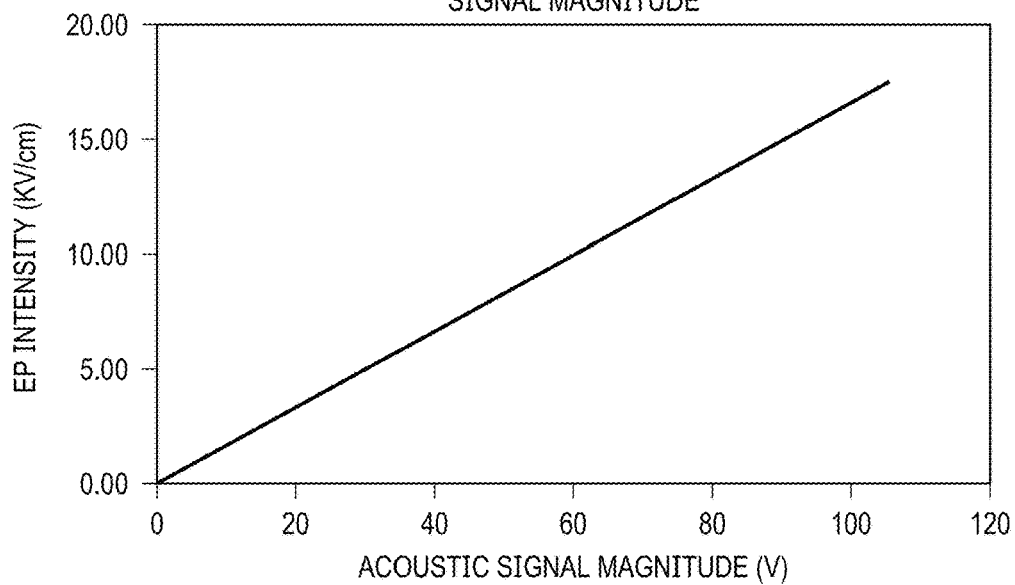
FIG. 4C is a graph of EP intensity versus acoustic signal magnitude.

FIG. 4B shows acoustic waves 410 detected when the electric field increases in intensity. As shown, an increase in the intensity of the electric field from 50 V to 1.2 kV increases the amplitude of the acoustic signal produced during μs EP exposure FIG. 4C is a graph 430 of EP intensity versus acoustic signal magnitude. The x-axis represents acoustic signal magnitude in V, and the y-axis represents EP intensity in kV/cm. The EP is a μs EP. The graph 430 demonstrates a linear acoustic signal corresponding to the voltage of the electric field. The largest amplitude of acoustic signal was obtained with the highest intensity of electric field.

These results support the use of EAT for in-situ monitoring during an electrotherapy procedure where the electric field utilized in the treatment also is used to induce acoustic signals, which allows for real-time construction of tomographic images during the electrotherapy procedure.

Example 3

Figure 5C:
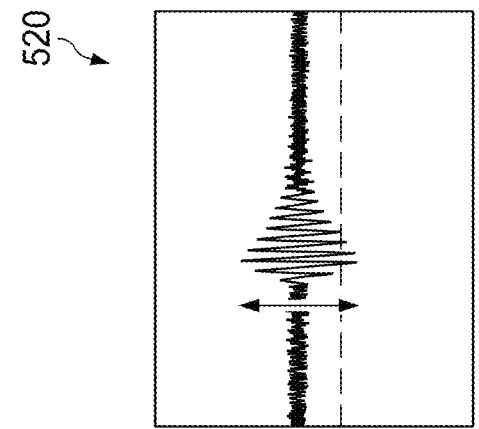
FIG. 5C shows an oscilloscope image of acoustic waves detected from exposure to an electric field at 1.2 kV and a 1 μs pulse width.
Figure 5B:
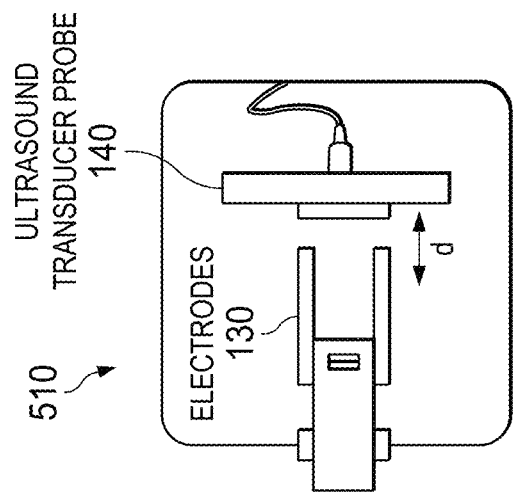
FIG. 5B is an image of a portion of the EAT system in FIG. 1 used as an experimental setup.
Figure 5A:
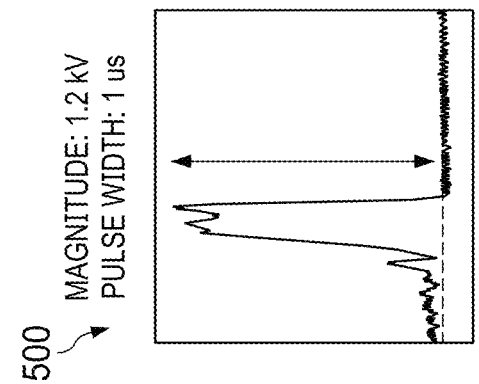
FIG. 5A shows an oscilloscope image of a high-voltage (1.2 kV) and short-pulse (1 μs) electric field.

FIG. 5A shows an oscilloscope image 500 of a high-voltage (1.2 kV) and short-pulse (1 μs) electric field. The electric field was measured using the ultrasound transducer probe 140, which was a high-voltage Tektronix P6015 operating at 1000×3 pF and a maximum of 40 kV.

FIG. 5B is an image of a portion 510 of the EAT system 100 in FIG. 1 used as an experimental setup. The portion 510 shows the electrodes 130 and the ultrasound transducer probe 140. The electrodes 130 are bipolar electrodes placed in distilled water, wherein the electric field is energized. The distilled water may also be deionized.

FIG. 5C shows an oscilloscope image 520 of acoustic waves detected from exposure to an electric field at 1.2 kV and a 1 μs pulse width.

Figure 5D:
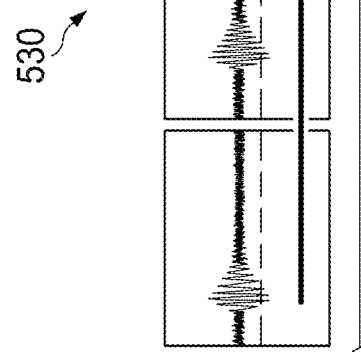
FIG. 5D shows oscilloscope images of the effect of electric field magnitude change (from 1.2 kV to 800 V) on acoustic signal magnitude during μs electric field exposure.

FIG. 5D shows oscilloscope images 530 of the effect of electric field magnitude change (from 800 V to 1.2 kV) on acoustic signal magnitude during μs electric field exposure. The acoustic waves are detected when the ultrasound transducer probe 140 is moved (at 1 μs, 1.2 kV EP).

The experimental setup in FIG. 5B was developed in order to generate acoustic signals based on electric fields utilized in electroporation techniques. FIG. 5B shows the feasibility of the experimental setup. Acoustic signals obtained in relation to the intensity of electric field are illustrated in FIG. 5C. By receiving and converting acoustic waves to electrical signals and then increasing the gain of the signal, these signals can be observed on an oscilloscope. The distance between the source (electric field distribution) and the ultrasound transducer probe 140 can be calculated by measuring the time between these generated acoustic signals from the electric field excitation. The source localization based on the sound emission movements is demonstrated in FIG. 5D. When the source of the electric field that has been applied to the electrodes 130 is moving in the media, the relative acoustic wave in response to electric field distribution is also moving "backward" and "forward" in time direction with the same pitch corresponding to electric field intensity. FIG. 5D shows a representative sample of responses, pictured in a sequential order of the resulting acoustic wave movements. Resulting acoustic signals when moving electric field location on a scale of 1 mm to 10 mm are demonstrated. The experimental results confirm the potential of applying this novel imaging technique for real-time monitoring of clinical applications using electroporation with the electric field distribution.

Example 4

Electroporation is medically used as a novel microsurgery tool using EPs as ECT, electrogenetherapy, and transdermal drug delivery. As demonstrated herein, the EAT system 100 and method disclosed herein can be used during an electroporation clinical application to provide low-cost, real-time imaging. This provides several features and benefits when characterizing the electric field distribution in membrane electroporation procedures with high-precision acoustic signals. Since the same electric field that is used for the electroporation process is used to induce acoustic signals, there is no need for an extra excitation source or other imaging modalities.

The method requires only applying an array of ultrasound transducer probes 140 and image reconstruction techniques based on the detected acoustic signals. Availability of an ultrasound machine in almost all clinics provides a unique opportunity to apply this new technique in real clinical applications. For example, the clinical technique known as ECT is a promising technique for local cancer tumor ablation. This technique is based on the local application of short and intensive EPs (non-thermal) that allows for delivery of non-permeant drugs to the cell interior.

Figure 6:
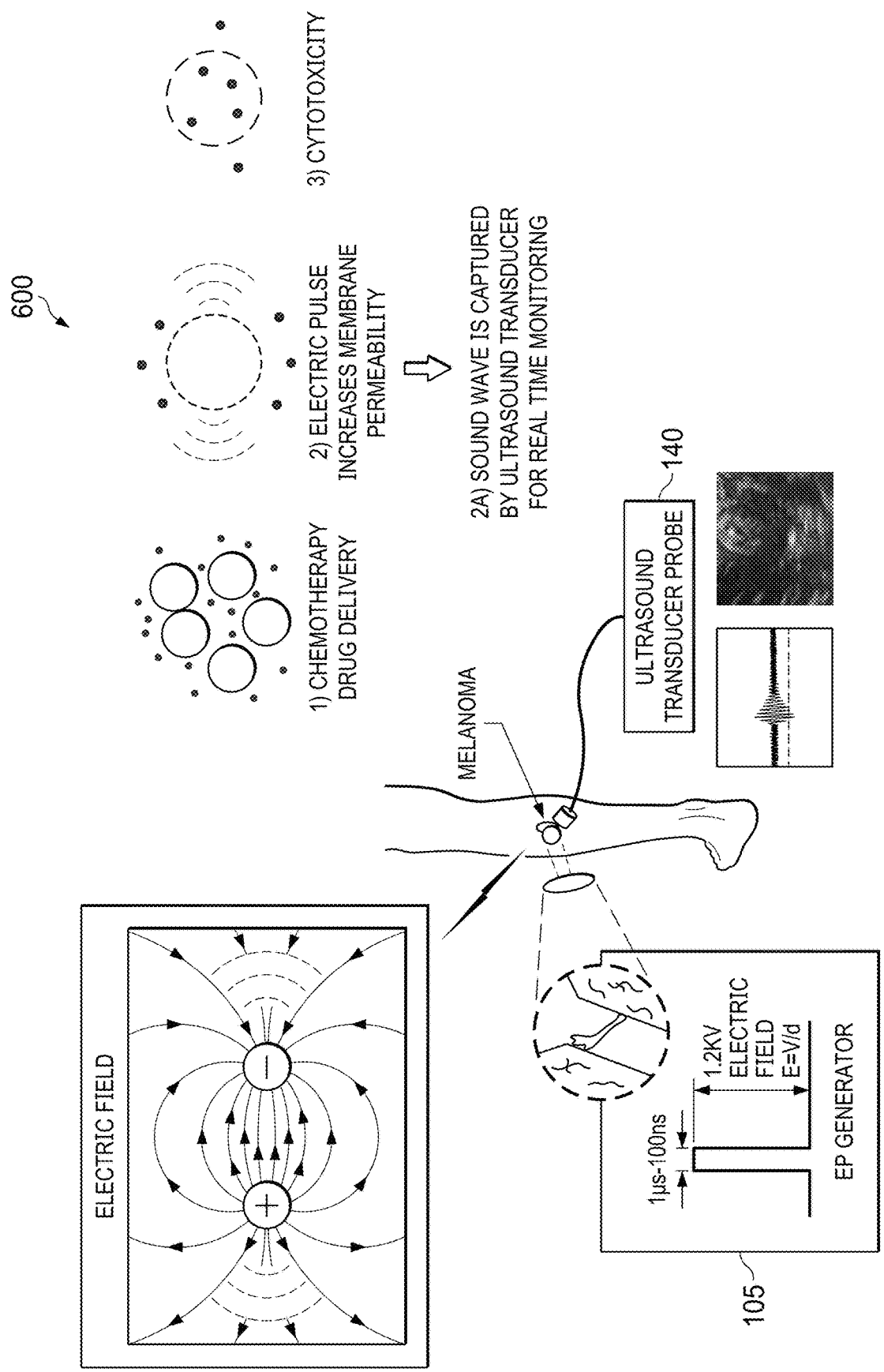
FIG. 6 shows a schematic design of an integrated ECT and EAT system for capturing acoustic signals generated during therapy.

FIG. 6 shows a schematic design 600 of an integrated ECT and EAT system for capturing acoustic signals generated during therapy. The schematic diagram 600 shows the EP generator 105 and the ultrasound transducer probe 140 from the EAT system 100 in FIG. 1. In this case, the EP generator 105 may generate ns Eps with magnitudes of 1.2 kV. The capturing enables real-time, in-situ monitoring of the electroporation ECT technique used, for example, to locally ablate tissue and treat tumors. The monitoring uses the same EP used for clinical treatment.

Example 5

Figure 8A:
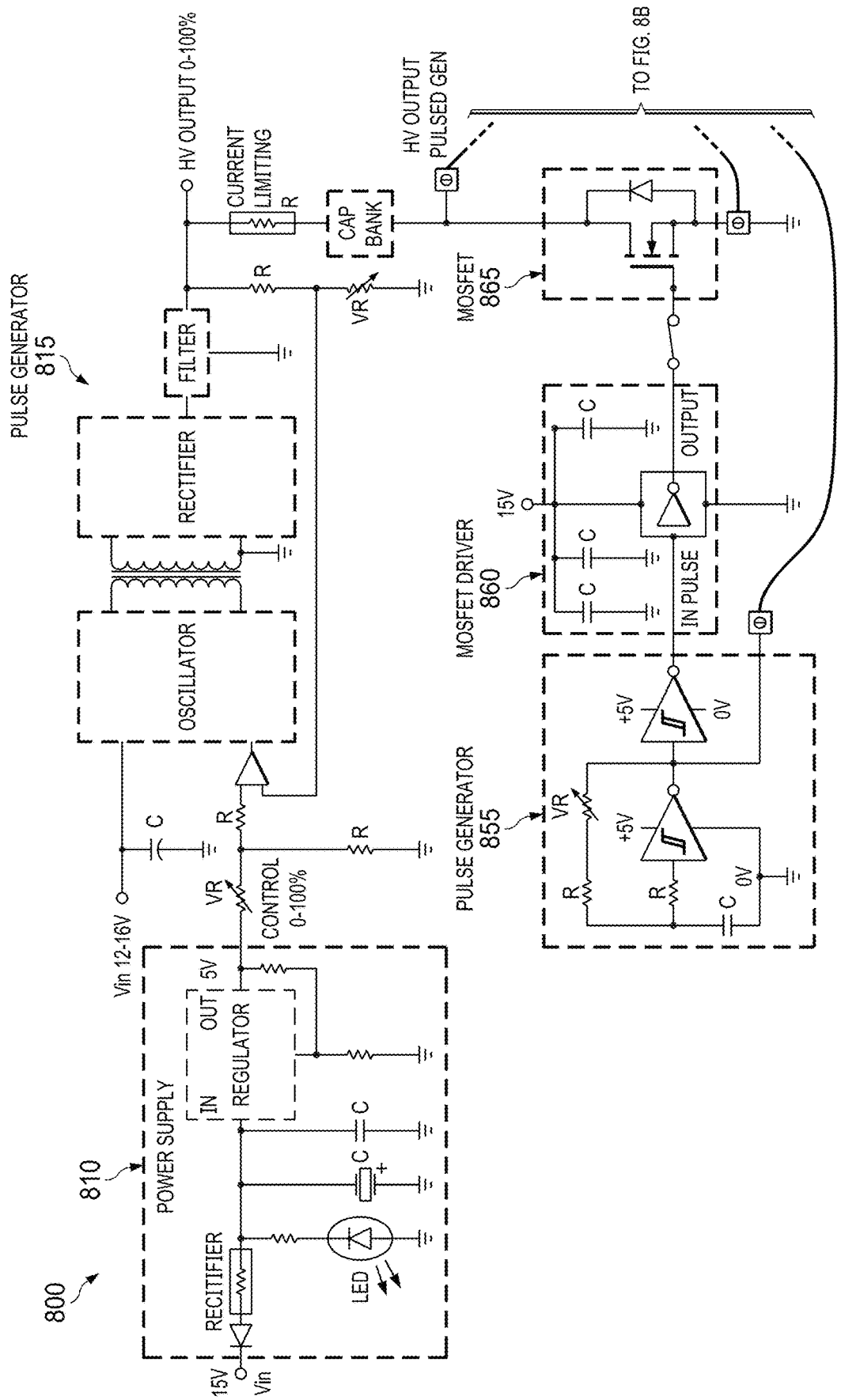
FIGS. 8A-8B show an EAT system constructed in accordance with the present disclosure.
Figure 8B:
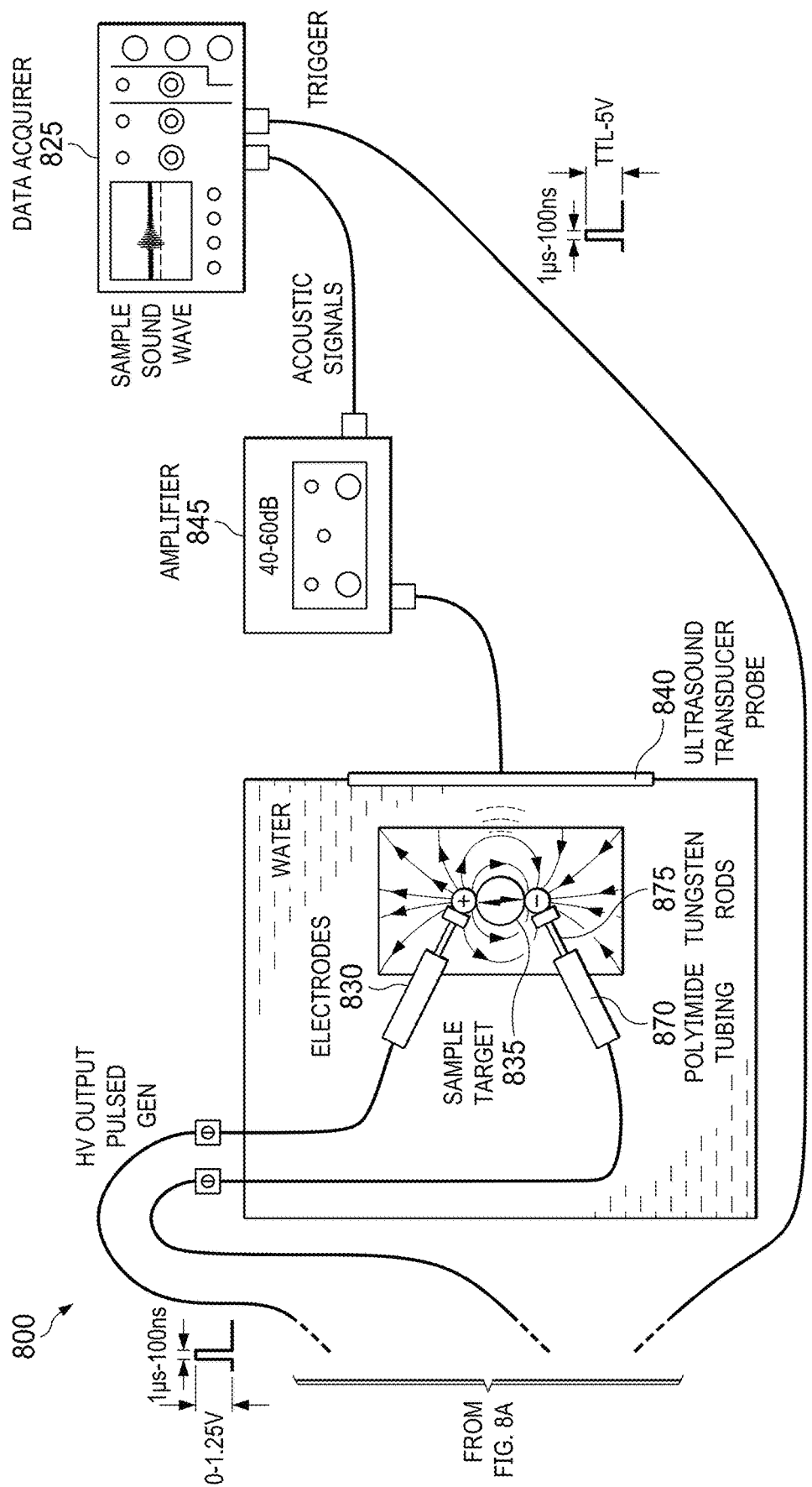

FIGS. 8A-8B show an EAT system 800 constructed in accordance with the present disclosure. The EAT system 800 is similar to the EAT system 100. Specifically, like the EAT system 100, the EAT system 800 comprises a power supply 810, a pulse generator 815, a data acquirer 825, electrodes 830, a sample target 835, an ultrasound transducer probe 840, and an amplifier 845. However, the EAT system 800 shows more components and sub-components than the EAT system 100. For instance, the EAT system 800 further comprises a pulse generator 855, a MOSFET driver 860, and MOSFET 865, and the EAT system 800 shows that the electrodes 830 comprise polyimide tubes 870 and tungsten rods 875.

Figure 8C:
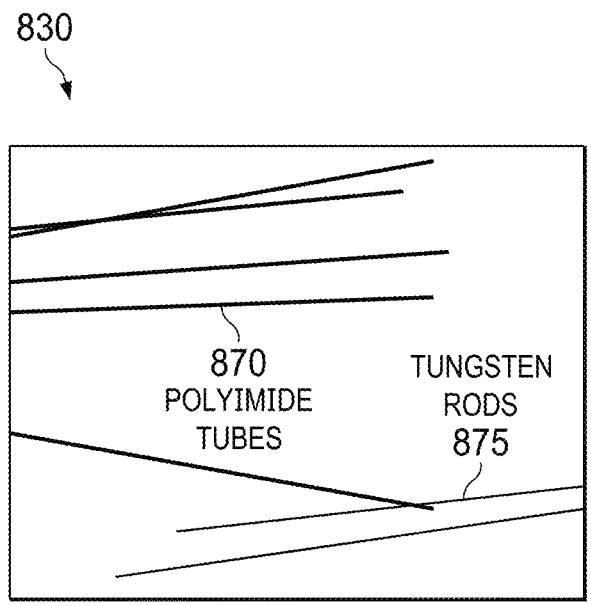
FIG. 8C shows the electrodes in FIG. 8B.

FIG. 8C shows the electrodes 830 in FIG. 8B. Specifically, FIG. 8C shows that the electrodes comprise the polyimide tubes 870 and the tungsten rods 875.

Figure 8D:
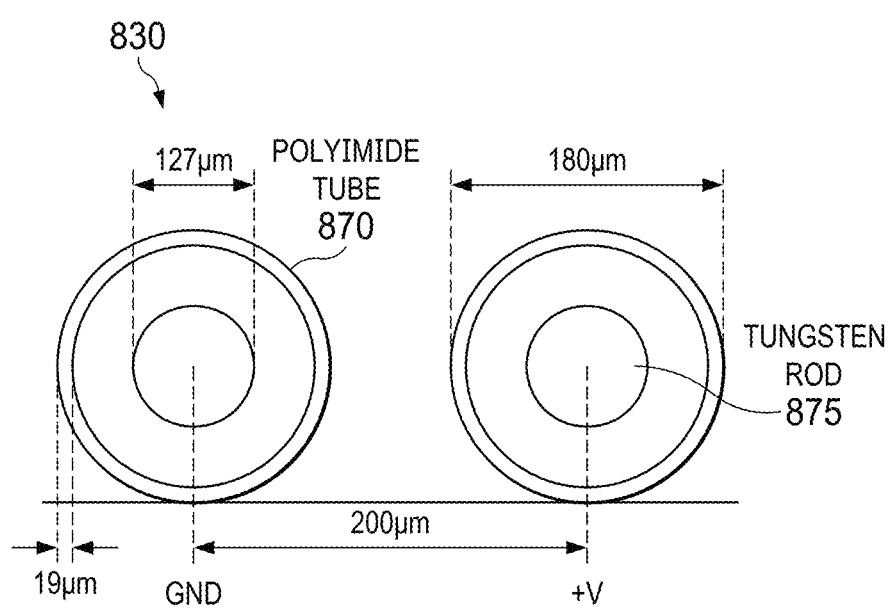
FIG. 8D shows the electrodes in FIG. 8B.

FIG. 8D shows the electrodes 830 in FIG. 8B. Specifically, FIG. 8D shows that the electrodes comprise the polyimide tubes 870 and the tungsten rods 875. FIG. 8D further shows dimensions of the electrodes.

The EAT system 800 produces electric fields with variable duration, polarity, and repetition rate by generating a TTL pulse (+5 Vpp) of 1 μs-100 ns duration to drive a high-speed, high-voltage MOSFET with very low crossover current that can be directly driven by an inverting MOSFET driver during high-voltage pulse sequencing. The MOSFET is connected to a high-voltage designated DC power supply converter with an adjustable 0-1250 Vp electric charge, a maximum current flow of 1 mA, and a maximal repetition frequency of 100 kHz. The inverting TTL pulse is also used for triggering ultrasonic signal acquisition with a minimum falling and rising time of 2.9 ns. The trimming custom potentiometers adjust the electric field intensity and duration. Next, an adjustable setup is designed to generate multiple electric fields with a series of voltage amplitudes at 1200 V, 1000 V, 800 V, 600 V, and 400 V, which are delivered by the electrodes 830. Multiple pulse widths from 1000 ns, 800 ns, 600 ns, 400 ns, 200 ns, and 100 ns with a mark-space ratio of less than 1 to 10000 are made using different TTL input signals that are connected to the high-voltage pulse sequencing via the n-channel MOSFET. The output voltage and current created during a μs-ns electric field is measured using a digital voltmeter, an ammeter, a passive high-voltage probe (Tektronix P6015, 1000×, and 3 pF), and an A/D digitizer (Oscilloscope-Tektronix TDS3054, with 5 Giga-samples/s). The high-intensity, ultra-short electric pulser is then connected to a micro-chamber electric-field distributer mounted on a side of the rectangular plastic tank (20×30×10 cm³). Then, agar-based high conductive phantoms (in scale of mS conductivity) were placed where the electrodes were inserted in the conductive phantom to characterize thermal and acoustic signals. These components are submerged in deionized water, which acts as a low-conductivity medium at room (25° C.) temperature for the propagation of sound in a homogeneous media. The micro-chamber electrode-field distribution comprises two bipolar tungsten rods 875 with circular cross section of 63.5 μm (A-M Systems) which are micro-fabricated using a glass Polyimide tubing 870 with an inside diameter of 180 μm and wall thickness of 19 μm. The tungsten rod 875 electrochemical properties are as 1.1432 g/amp-hr, 4.55 eV, heat fusion of 35.4 kH/mol, thermal expansion of 4.6 E-6 cm/cm/° C., electrical conductivity of 0.189 E+6 S/cm, thermal conductivity of 1.74 W/cmK. The distance between the two microscale electrodes 830 influences the intensity of the electric field and can be varied to study the effect of the electric field distribution on the acoustic signal. A bipolar setup of two electrodes 830 at a distance (d) of approximately 200 μm was used to produce an electric potential distribution of 63 kVcm-1 to 20 kVcm$^{-1}$ using a voltage-to-distance ratio E=V/d, which is a typical electric field exposure used in clinical electrotherapy. A delivery system was designed to directly change the location of the electric field distribution that induces different acoustic signals in a conductive media. In this delivery system, the micro-chamber electrodes 830 are moved along 3 directions (x, y, z-axes) in the media in millimeter increments.

Mathematical Model

For electroacoustic emission, short and intense EPs are applied to biological tissues. Some of the applied electrical energy will be absorbed and converted into heat energy, leading to transient temperature rise and subsequent thermoelastically-induced initial pressure rise. The pulse duration must be sufficiently short so as to satisfy thermal and stress confinement. When thermal confinement and stress confinement are satisfied, heat conduction and stress propagation are negligible during the voltage pulse. Thus, the initial electroacoustic (EA) pressure rise $p_0(r)$ can be obtained by:

$$p_0(r) = \frac{\beta \Delta T(r)}{\kappa} \quad (1)$$

where β denotes the thermal coefficient of volume expansion (K$^{-1}$), ΔT(r) denotes the change in temperature (K), and κ denotes the isothermal compressibility (Pa$^{-1}$).

If the voltage pulse width is short enough, thermal diffusion can be neglected. The time derivative of the temperature $\dot{T}(r)$ is then given by:

$$\dot{T}(r) = \frac{1}{\rho C_v} \dot{Q}(r) \quad (2)$$

where $\dot{Q}(r)$ is the absorbed electrical power density (absorbed power per unit volume). This function is the time derivative of the heat absorbed per unit volume Q. ρ is the mass density (g/m³), and $C_v$ is the specific heat capacity at constant volume (J/gK). $\dot{Q}(r, t)$ can be expressed using the vector form of Joule's law:

$$\dot{Q}(r) = \frac{dP}{dv} = \vec{J} \cdot \vec{E} \quad (3)$$

where $\vec{E}$ represents the electric field, $\vec{J}$ represents the current density, P is the power, and v is volume. The vector form of Ohm's law is stated as:

$$\vec{J} = \sigma \vec{E} \quad (4)$$

where σ is the specific electrical conductivity (S/m). Combining equations (3) and (4) yields:

$$\dot{Q} = \sigma \vec{E} \cdot \vec{E} = \sigma |\vec{E}|^2 \quad (5)$$

Noting that the gradient of the potential V(r) yields the electric field, the following results:

$$\dot{Q} = \sigma |\nabla V|^2 \quad (6)$$

In the case of delta function heating, the temperature change ΔT is given from equations (2) and (6) as follows:

$$\Delta T = \frac{Q}{\rho C_V} = \frac{\sigma |\nabla V|^2 t_L}{\rho C_V} \qquad (7)$$

where $t_L$ is the pulse width of the electric field. Combing equations (1) and (7) yields:

$$p_0(r) = \frac{\beta \Delta T}{\kappa} = \frac{\beta \sigma |\nabla V|^2 t_L}{\kappa} \qquad (8)$$

Therefore, equation (8) shows the relationship between the initial electroacoustic pressure, the input electrical voltage, pulse duration, and electrical conductivity of the soft tissue. Thus, by detecting the acoustic emission induced by the pulsed electric field, information about the electric field distribution during the electrotherapy delivery is revealed.

The electroacoustic signal generation and propagation can be modeled by the following wave equation:

$$\left(\nabla^2 - \frac{1}{v_s^2}\frac{\partial^2}{\partial t^2}\right)p(r,t) = -\frac{\beta}{\kappa v_s^2}\frac{\partial^2 T(r,t)}{\partial t^2} \qquad (9)$$

where $v_s$ is the speed of sound, p(r, t) denotes the acoustic pressure generated by the absorbed electric energy at location r and time t. T(r) denotes the temperature rise, κ denotes the isothermal compressibility, and β denotes the thermal coefficient of volume expansion. The temperature rise T (r, t) is determined by the heating function Q (r, t) as follows:

$$\rho C_v \frac{\partial T(r,t)}{\partial t} = \lambda \nabla^2 T(r,t) + Q(r,t) \qquad (10)$$

λ is the thermal conductivity, and Q (r, t) is directly related to the input electrical voltage, pulse duration, and electrical conductivity of the soft tissue based on equation (6). Furthermore:

$$Q(r,t) = \eta_{th} A_e(r,t) \qquad (11)$$

where $\eta_{th}$ is the percentage of absorbed electric energy converted into heat. Assuming thermal confinement is satisfied by a μs-ns EP, the wave equation can be rewritten as follows:

$$\left(\nabla^2 - \frac{1}{v_s^2}\frac{\partial^2}{\partial t^2}\right)p(r,t) = -\frac{\beta}{C_P}\frac{\partial A_e(r,t)}{\partial t} \qquad (12)$$

Then the acoustic pressure p(r, t) generated by the electric field at the transducer position r and time t can be determined by the following equation:

$$p(r,t) = \frac{1}{4\pi v_s^2}\int dr' \frac{1}{|r-r'|}\Gamma \eta_{th}\frac{\partial A_e(r',t')}{\partial t'}\bigg|_{t'=t-\frac{|r-r'|}{v_s}} \qquad (13)$$

where Γ is the unit-less Grüneisen parameter defined as $$\Gamma = \frac{\beta}{\kappa \rho C_p}.$$

This is an acoustic pressure wave that can be detected by the ultrasound transducer probe 140 and thus provide real-time feedback of electrotherapy without the need for an additional source.

For determining the acoustic signals induced from the electrical energy, looking at equation (1), the local pressure rise is the cause of the temperature variation based on the electrical conductivity and thermal conductivity of the tissue sample under test, for instance a fatty breast tissue or a normal breast tissue. Considering a voltage of 700 V applied in pulses of 1 μs to a fatty breast tissue that has a thermal coefficient of Cv=2.43 J/gK, a mass density of ρ=0.934 g/cm³, and an electrical conductivity of 4 mS/cm (R=250Ω) at 1 MHz ($t_L$=1 μs pulse), the change of temperature ΔT in the case of delta function heating, is given by equation (7) and is about 0.863 mK as follows:

$$\Delta T = \frac{Q}{\rho C_V} t_L$$

$$= \frac{(700)^2 (v^2)}{250\,\Omega \times 0.934 \left(\frac{J}{gK}\right) \times 2.43(g)} \times 1\,\mu s$$

$$= 863.580\,K \frac{v}{\Omega} \cdot v \cdot \frac{1}{J} \cdot \mu s$$

$$= 863.580\,\frac{K.watt.\mu s}{J}$$

$$= 0.863\,mK.$$

Knowing ΔT, then the pressure $p_0(r)$ is solved as follows:

$$p_0(r) = \frac{\text{thermal coefficient of volume} \times 0.863\,\text{mK}}{\text{speed of sound on the medium}}.$$

This temperature variation seems enough to produce acoustic signals. It has been demonstrated that an approximately 1 mK temperature rise results in an 800 Pa pressure rise, which is above the noise level of a typical ultrasound transducer probe like the ultrasound transducer probe 140.

The mathematical model predicts a dependence of the amplitude of the induced acoustic signal and conductivity of the sample under test. In addition, the experiments confirm the linearity of the acoustic signal with respect to various conductive media. However, the experiments may not be strictly linear due to thermal noise interfering with the relatively weaker acoustic signal. Amplification of the acoustic signal may address that issue, though the amplification may also be non-linear, thus providing non-ideal measurements.

The real-time output emission signals correlated to electric field distributions represent real-time imaging data. This unique real-time imaging technique provides valuable information for irreversible and reversible electroporation. This technique can be used to define, or identify, the most effective electroporation or other electrotherapy area in order to avoid or mitigate damage to surrounding cells. This also provides real-time information associated with electric field delivered at the sample target 135 to determine electrode 130 size and the intensity of electric field distribution for tissue ablation in cancer tumors. In addition, this real-time imaging information can also be used for the prediction of electroporation techniques, which is required in treatment plans by verifying the accuracy of the outcomes. Therefore, applying this new real-time imaging technique in current electroporation-based applications provides a complementary technique for use in clinical settings.

In the above embodiments, a localized DC electric field up to 63 kV/cm has been used and can be increased up to 100 kV/cm by changing the electrode 130 distance. A mark to space ratio of 1/10000, which is 10 kHz, has been used, and the EAT system 100 can be operated within the frequency range from 1 kHz to 100 kHz. The experiment on irreversible and reversible cell electroporation can flow through a localized DC electric field.

Figure 7:
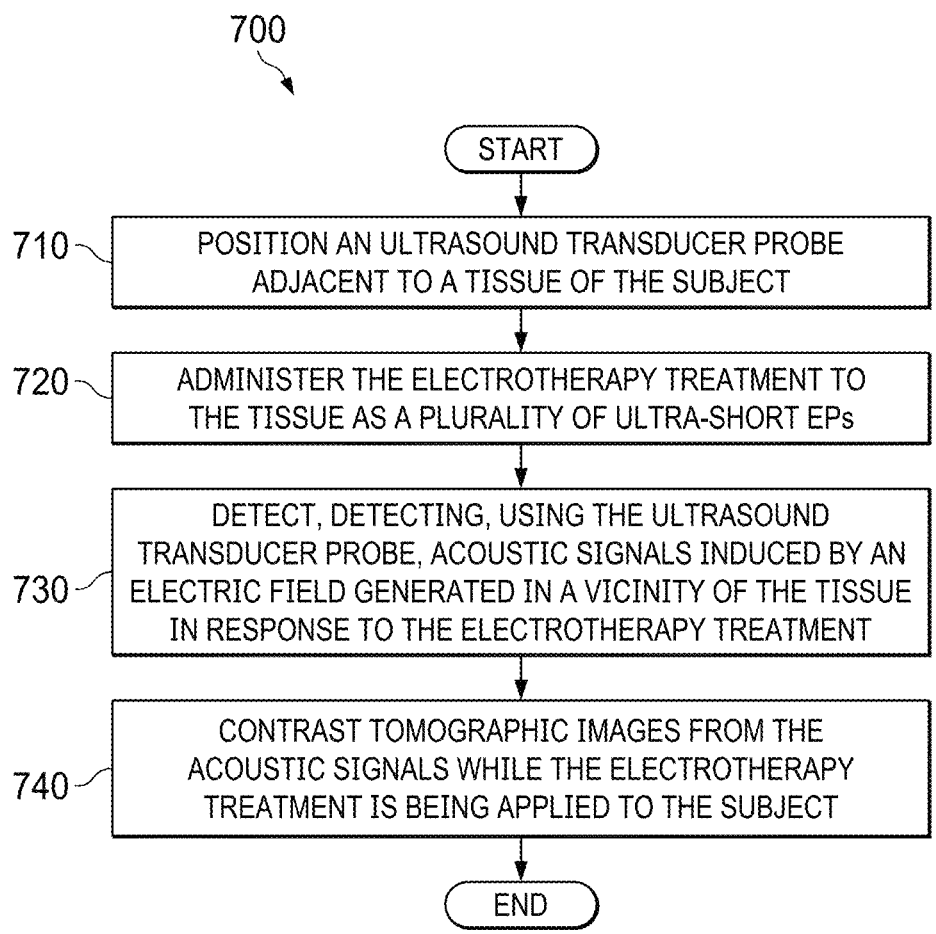
FIG. 7 is a flowchart illustrating a method of monitoring an electrotherapy treatment applied to a subject in need of such treatment according to an embodiment of the disclosure.

FIG. 7 is a flowchart illustrating a method 700 of monitoring an electrotherapy treatment applied to a subject in need of such treatment according to an embodiment of the disclosure. A physician or a technician may perform the method 700. At step 710, an ultrasound transducer probe is positioned adjacent to a tissue of a subject. For instance, a physician places the ultrasound transducer probe 140 adjacent to the sample target 135, and the sample target 135 is a tissue of a human. Specifically, the sample target 135 may be a tumor or an area of tissue comprising the tumor.

At step 720, the electrotherapy treatment is administered to the tissue as a plurality of ultra-short EPs. For instance, the physician administers the electrotherapy treatment using the EP generator 105 and the electrodes 130. The electrotherapy treatment is electroporation, ECT, or muscular electrostimulation. The ultra-short EPs are in a range of 1 ps-100 µs, have a voltage intensity in a range of 1 V-5 kV, and have a frequency in a range of 1 Hz-100 kHz.

At step 730, acoustic signals induced by an electric field are detected using the ultrasound transducer probe. The electric field is generated in a vicinity of the tissue in response to the electrotherapy treatment. For instance, the physician detects the acoustic signals using the ultrasound transducer probe 140. The acoustic signals may be similar to the acoustic signals in FIGS. 3, 4A, 4B, 5C, and 5D.

Finally, at step 740, tomographic images are constructed from the acoustic signals while the electrotherapy treatment is being applied to the subject. The tomographic images represent a location of the electric field in the tissue. The constructing in step 740 may be in real time during the administering in step 720.

The method 700 may comprise additional steps. For instance, the electrotherapy treatment is modified based on the tomographic images. The modifying comprises additional steps. For instance, a most effective area of the tissue for the electrotherapy treatment is identified based on the tomographic images. Administration of the electrotherapy treatment is continued to only the most effective area in order to avoid or mitigate damage to surrounding cells of the tissue.

While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods. Changes may be made in various aspects of the methods described herein without departing from the spirit and scope of the present disclosure.

What is claimed is:

1. A method of monitoring an electrotherapy treatment applied to a subject in need of such treatment, the method comprising:
   positioning an ultrasound transducer probe adjacent to a tissue of the subject;
   administering the electrotherapy treatment to the tissue as a plurality of ultra-short electric pulses (EPs) at a specified voltage intensity or a specified pulse width;
   detecting, using the ultrasound transducer probe, acoustic signals induced by an electric field generated in a vicinity of the tissue in response to the electrotherapy treatment;
   constructing tomographic images from the acoustic signals while the electrotherapy treatment is being applied to the subject, wherein the tomographic images indicate locations of the electric field in the tissue;
   repositioning the electrotherapy treatment based on a first location of the electric field represented in the tomographic images and defining a sample target; and
   adjusting a voltage intensity of the ultra-short EPs away from the specified voltage intensity and to an adjusted voltage intensity based on a real-time requirement and based on the first location, or adjusting a pulse width of the ultra-short EPs away from the specified pulse width and to an adjusted pulse width based on the real-time requirement and based on the first location,
   wherein the adjusted voltage intensity is non-zero and different from the specified voltage intensity, and
   wherein the adjusted pulse width is non-zero and different from the specified pulse width.

2. The method of claim 1, wherein the electrotherapy treatment is electroporation.

3. The method of claim 1, wherein the electrotherapy treatment electrochemotherapy (ECT).

4. The method of claim 1, wherein the electrotherapy treatment is muscular electrostimulation.

5. The method of claim 1, wherein the ultra-short EPs are in a range of 1 picosecond (ps) to 100 microseconds (µs).

6. The method of claim 1, wherein the voltage intensity is in a range of 1 volt (V) to 4 V.

7. The method of claim 1, wherein the ultra-short EPs have a frequency in a range of 1 Hertz (Hz) to 100,000 Hz.

8. An electric-field-inducted acoustic tomography (EAT) system comprising:
   an electric pulse (EP) generator configured to generate a plurality of ultra-short EPs;
   electrodes coupled to the EP generator and configured to administer an electrotherapy treatment to a tissue of a subject via the ultra-short EPs at a specified voltage intensity or a specified pulse width;
   an ultrasound transducer probe configured to detect acoustic signals induced by an electric field generated in the tissue of the subject in response to the electrotherapy treatment; and
   a tomographic imager configured to construct tomographic images from the acoustic signals induced by the electric field,
   wherein the tomographic images represent the electric field,
   wherein the tomographic imager is configured to construct the tomographic images during the electrotherapy treatment to enable monitoring of the electrotherapy treatment, and wherein the EAT system is configured to:
enable repositioning of the electrotherapy treatment based on a location of the electric field indicated in the tomographic images and defining a sample target; and
enable adjusting of a voltage intensity of the ultra-short EPs away from the specified voltage intensity and to an adjusted voltage intensity based on a real-time requirement and based on the location, or enable adjusting a pulse width of the ultra-short EPs away from the specified pulse width and to an adjusted pulse width based on the real-time requirement and based on the location,
wherein the adjusted voltage intensity is non-zero and different from the specified voltage intensity, and
wherein the adjusted pulse width is non-zero and different from the specified pulse width.

9. The EAT system of claim 8, wherein the ultrasound transducer probe is configured to convert the acoustic signals into electrical signals, and wherein the EAT system further comprises an amplifier coupled to the ultrasound transducer probe, the amplifier configured to amplify the electrical signals to create amplified electrical signals.

10. The EAT system of claim 9, further comprising a data acquirer coupled to the EP generator, the amplifier, and the tomographic imager and configured to synchronize the ultra-short EPs with the acoustic signals.

11. The EAT system of claim 8, wherein the ultrasound transducer probe is positioned adjacent to the tissue of the subject.

12. The EAT system of claim 8, wherein the electrotherapy treatment is electroporation.

13. The EAT system of claim 8, wherein the electrotherapy treatment is electrochemotherapy (ECT).

14. The EAT system of claim 8, wherein the electrotherapy treatment is muscular electro-stimulation.

15. The EAT system of claim 8, wherein the ultra-short EPs are in a range of 1 picosecond (ps) to 100 microseconds (μs).

16. The EAT system of claim 8, wherein the voltage intensity is in a range of 1 volt (V) to 4 V.

17. The EAT system of claim 8, wherein the ultra-short EPs have a frequency in a range of 1 Hertz (Hz) to 100,000 Hz.

18. The method of claim 1, wherein the electrotherapy treatment is ablation for cancer.

19. A method for monitoring an electrotherapy treatment applied to a subject in need of the electrotherapy treatment, wherein the method comprises:
administering the electrotherapy treatment to the subject using ultra-short electric pulses (EPs) at a specified voltage intensity or a specified pulse width, wherein the electrotherapy treatment is electroporation therapy;
performing electroacoustic imaging on the subject;
using the electroacoustic imaging to perform a real-time monitoring and a real-time guidance of the electroporation therapy;
obtaining, with no additional source or add-on imaging modality, a real-time critical feedback in response to using the electroacoustic imaging to perform the real-time monitoring and the real-time guidance of the electroporation therapy;
repositioning the electrotherapy treatment based on a location of an electric field indicated in tomographic images and defining a sample target; and
adjusting a voltage intensity of the ultra-short EPs away from the specified voltage intensity and to an adjusted voltage intensity based on a real-time requirement and based on the location, or adjusting a pulse width of the ultra-short EPs away from the specified pulse width and to an adjusted pulse width based on the real-time requirement and based on the location,
wherein the adjusted voltage intensity is non-zero and different from the specified voltage intensity, and
wherein the adjusted pulse width is non-zero and different from the specified pulse width.

20. The method of claim 1, further comprising further adjusting the voltage intensity by increasing the voltage intensity.

21. The method of claim 1, wherein the sample target is a tumor.

22. The method of claim 1, wherein the tomographic images further indicate a change in dielectric characteristics of the tissue.

23. The method of claim 1, further comprising continuing the electrotherapy treatment to only a most effective area of the tissue in order to avoid or mitigate damage to surrounding cells of the tissue.

24. The method of claim 1, further comprising further repositioning the electrotherapy treatment to areas of the tissue with no electroporation or incomplete electroporation.

25. The method of claim 1, further comprising further administering the electrotherapy treatment by placing electrodes at different distances from the tissue.

26. The method of claim 1, wherein the tomographic images are based on a dependence of an amplitude of the acoustic signals and a conductivity of the tissue.

27. The EAT system of claim 8, wherein the electrodes have sizes configured to administer tissue ablation of cancer cells.

28. The method of claim 19, wherein the electrotherapy treatment is electroporation.

29. The method of claim 19, wherein the electrotherapy treatment is electrochemotherapy (ECT).

30. The method of claim 19, wherein the electrotherapy treatment is muscular electrostimulation.

* * * * *